(12) United States Patent
Konowalchuk et al.

(10) Patent No.: US 7,399,790 B2
(45) Date of Patent: Jul. 15, 2008

(54) VIRUCIDAL COMPOSITIONS

(76) Inventors: Thomas W. Konowalchuk, 1070 NE. 7th Dr., Newport, OR (US) 97365; Jack Konowalchuk, 1098 NE. 7th Dr., Newport, OR (US) 97365

( * ) Notice: Subject to any disclaimer, the term of this patent is extended or adjusted under 35 U.S.C. 154(b) by 0 days.

(21) Appl. No.: 09/795,279

(22) Filed: Feb. 28, 2001

(65) Prior Publication Data

US 2002/0165277 A1 Nov. 7, 2002

(51) Int. Cl.
*A01N 37/00* (2006.01)
*A01N 33/18* (2006.01)
*A01N 33/24* (2006.01)

(52) U.S. Cl. .................. 514/724; 514/557; 514/739

(58) Field of Classification Search .............. 514/739, 514/557, 724
See application file for complete search history.

(56) References Cited

U.S. PATENT DOCUMENTS

| | | | |
|---|---|---|---|
| 4,513,008 A | 4/1985 | Revici et al. ............... 514/560 |
| 4,647,458 A | 3/1987 | Ueno et al. | |
| 4,975,217 A | 12/1990 | Brown-Skrobot et al. ... 252/107 |
| 5,043,357 A | 8/1991 | Hoffler et al. ............... 514/553 |
| 5,071,650 A | 12/1991 | Dove et al. ................. 424/85.8 |
| 5,385,938 A * | 1/1995 | Yu et al. | |
| 5,405,602 A | 4/1995 | Simmons et al. | |
| 5,492,932 A | 2/1996 | Kundsin | |
| 5,512,200 A | 4/1996 | Garcia ....................... 252/142 |
| 5,531,984 A * | 7/1996 | Staats | |
| 5,534,554 A | 7/1996 | Katz et al. .................. 514/724 |
| 5,728,404 A | 3/1998 | von Rheinbaben et al. .. 424/642 |
| 5,767,163 A | 6/1998 | Kundsin ..................... 514/642 |
| 5,952,392 A | 9/1999 | Katz et al. .................. 514/724 |
| 6,034,133 A | 3/2000 | Hendley ..................... 514/573 |
| 6,858,232 B2 | 2/2005 | Verbiscar | |
| 7,045,548 B2 | 5/2006 | Konowalchuk et al. | |
| 7,279,163 B1 | 9/2007 | Konowalchuk et al. | |
| 2002/0165279 A1 | 11/2002 | Konowalchuk et al. | |
| 2006/0210648 A1 | 9/2006 | Konowalchuk et al. | |

FOREIGN PATENT DOCUMENTS

| AM | 200300843 | 6/2005 |
|---|---|---|
| AU | 2002251933 | 1/2008 |
| AZ | 200300843 | 6/2005 |
| BR | PI0207703-5 | 10/2004 |
| BY | 200300843 | 6/2005 |
| CA | 1 221 640 * | 5/1987 |
| CA | 2439413 | 9/2002 |
| CN | 2809063.2 | 7/2006 |
| EA | 200300843 | 6/2005 |
| EP | 2720972.5 | 2/2004 |
| GB | 2 187 097 A | 9/1987 |
| GB | 2187097 | 9/1987 |
| JP | 11087290 * | 3/1999 |
| KG | 200300843 | 6/2005 |
| KZ | 200300843 | 6/2005 |
| MA | 27326 | 12/2004 |
| MA | 27326 | 1/2005 |
| MD | 200300843 | 6/2005 |
| NZ | 527931 | 6/2006 |
| RU | 200300843 | 6/2005 |
| SG | 200304677-8 | 3/2006 |
| TJ | 200300843 | 6/2005 |
| TM | 200300843 | 6/2005 |
| WO | WO 00/62613 | 10/2000 |
| WO | WO 2000/062613 | 10/2000 |
| WO | WO 2002/069887 | 9/2002 |

OTHER PUBLICATIONS

Bhatia et al., Indian Journal of Animal Sciences 1998; 68(6): 518-520.*
Wenninger, International Cosmetic Ingredient Dictionary and Handbook, 7th ed., vol. 1, pp. 163-168.*
English abstract of Ota et al. (JP 11087290).*
English Translationo f JP 11-87290.*
Merck Index, 11th ed., 1989, p. 707, monograph 4394.*
Lueck, Antimicrobial Food Additives, 1980, published by Springer-Verlag, pp. 136-139, 159-165, and 167-173.*
Milton B. Dobkin, et al. "Virucidal Efficacy of Saturated Intermediate Length Straight-chain Alcohols in Biologically Active Protein Solutions," *Biologicals* (1991) 19: 177-185.
G. Poli, et al. "Virucidal Activity of Organic Acids", *Food Chemistry*, (1979) 4: 250-258.
Wallace Snipes, et al. "Inactivation of Lipid-Containing Viruses by Long-Chain Alcohols," *Antimicrobial Agents and Chemotherapy* (1977) 11: 98-104.
Jack Konowalchuk, Joan I. Speirs, "Virus Inactivation by Grapes and Wines," *Applied and Environmental Microbiology* (1976) 32: 757-763.
PCT International Search Report dated Sep. 18, 2002 issued in PCT/US/2002/04273 (WO 2002/069887).
PCT Written Opinion dated Oct. 24, 2003 issued in PCT/US/2002/04273 (WO 2002/069887).
PCT Preliminary Examination Report dated Dec. 19, 2003 issued in PCT/US/2002/04273 (WO 2002/069887).

(Continued)

*Primary Examiner*—San-ming Hui
(74) *Attorney, Agent, or Firm*—Weaver Austin Villeneuve & Sampson LLP; Tom Hunter

(57) ABSTRACT

A method of inactivating enveloped virus comprises contacting said virus with a virucidally effective amount of a composition comprising a C1 to C3 monohydroxy alcohol or a C3 to C4 diol and a sufficient amount of an acid to adjust the pH of the composition to below 4.6. Topical administration of the composition is preferred and is effective in treating lesions associated with herpes infections. Pharmaceutical compositions for use in the present method are provided.

7 Claims, No Drawings

OTHER PUBLICATIONS

Australian Office Action dated May 11, 2006 in related Australian Patent App. No. 2002251933.
Chinese Office Action dated Jun. 10, 2005 in Chinese App. No. 02809063.2.
Chinese Certificate of Invention Patent No. 274143 issued on Jul. 19, 2006.
Eurasian Certificate of Patent No. 005917 dated Jun. 30, 2005.
European Search Report dated Feb. 16, 2004 in related EP App. 2720972.5.
European Office Action dated Apr. 28, 2006 in related EP App. 2720972.5.
Israel—Notice of Office Action dated Jun. 27, 2007 in related Israeli App. No. 157596.
Mexico—Notice of Office Action dated May 7, 2007 in related Mexican App. No. PA/a/2003/007748.
New Zealand Office Action dated Mar. 8, 2005 in related New Zealand App. No. 527931.
Philippine Office Action dated Jun. 23, 2006 in related Philippine App. No. 1-2003-500789.
Singapore—Certificate of Grant dated Mar. 31, 2006 for Singapore Patent No. 98871.
European Search Report, Feb. 15, 2004.

* cited by examiner

VIRUCIDAL COMPOSITIONS

BACKGROUND OF THE INVENTION

1. Field of the Invention

The present invention relates to a virucidal composition having activity against enveloped viruses, and specifically to topical compositions having virucidal activity against viruses of the Herpes family.

2. Description of the Prior Art

Pathogenic viruses can be classified into two general types with respect to the viral structure, those that contain lipids and those that do not. Some well known lipid-containing pathogenic viruses, known as "enveloped" viruses, include herpes virus, e.g., herpes simplex 1 and 2; myxovirus, e.g., influenza virus; paramyxovirus, e.g., virus responsible for measles and mumps, and respiratory syncitial virus responsible for croup; corona virus, which is also implicated in the common cold; and toga virus, e.g., rubella virus and virus responsible for encephalitis and hemorrhagic fever. Many other pathogenic viruses lack an outer envelope, and therefore are characterized as "naked" viruses. Included in this category are the rhinovirus (the principle causative agent of the "common cold"; influenza viruses, polioviruses, and adenoviruses.

Viral infections cause considerable discomfort, disease and can be fatal. Viruses such as cytomegalovirus (CMV), human lymphotrophic viruses (e.g., HTLV-1) and human immunodeficiency viruses (e.g., HIV-1) result in significant morbidity and mortality. Herpes simplex viruses (HSV-1 and HSV-2) are associated with inflammation and lesions of the skin and mucosal membranes, including cold sores, fever blisters and genital herpes lesions. Varicella-zoster virus (VZV) causes chicken pox and shingles, and Epstein-Barr virus (EBV) is associated with mononucleosis. Influenza viruses cause flu symptoms and can be fatal. HIV causes acquired immunodeficiency which debilitates and kills infected individuals. Although these viruses may remain latent in some cells and for varying periods of time, generally viral replication results in irreversible destruction of the infected cell producing different clinical manifestations of the diseases they cause.

Herpes simplex infections occur and recur at many areas and organs of the body, but particularly the skin and mucocutaneous areas. Roughly 50 million Americans suffer from fever blisters or cold sores with more than 100 million episodes estimated annually. The medical term for the condition is recurrent herpes simplex labialis. It is caused by the herpes simplex virus (HSV) which, following a primary infection, takes up permanent life-long residence and lies dormant in the nerve ganglia. Upon reactivation by various stimuli, the virus travels along nerve pathways towards the lips and mouth where it emerges as a lesion or blister. The disfiguring lesions typically last 7 to 10 days. Other common sites for outbreaks caused by HSV include anywhere on the skin such as the ears, nose, chest, abdomen, arms, palms, dorsa of the hands, fingers, thighs and legs. Other common sites are the eyes and cervix. Less often involved but observed are the mouth, respiratory tract and central nervous system.

It is known in the art that quaternary ammonium compounds such as benzalkonium chloride are effective against bacteria but are not virucidal. In Hendley et al., (Antimicrobial Agents and Chemotherapy, 14:690-694 (1978)) foams containing ethyl alcohol, benzalkonium chloride (BAK), and hexachlorophene were evaluated. Ethyl alcohol alone was not effective, and the combination of ethyl alcohol with BAK was fairly ineffective in killing rhinoviruses.

It is known in the art that "enveloped" viruses are relatively sensitive and, thus, can be inactivated by virucidal disinfectants known so far. In contrast, greater problems are caused by naked viruses, which are substantially more stable against conventional disinfectants and which can be inactivated only with relatively high concentrations of formaldehyde. However, formaldehyde is undesirable because of toxicity and does not allow the disinfection of contaminated parts of the body to be effected in either the clinic or the laboratory.

Poli, et al. ("Virucidal Activity of Organic Acids" Food Chem. (England) 4(4)251-8 (1979)) describe a study of the virucidal action of organic acids (citric, malic, etc.). These workers found that citric, malic, pyruvic and succinic acids, among others, were effective in vitro against "enveloped" viruses (herpesvirus, orthomyxovirus and rhabdovirus (Rabies virus)). Their experiments were carried out at room temperature with aqueous solutions of pure acids. No substrate or carrier was used. The three viruses chosen for study by these workers were all "enveloped" viruses. Poli, et al. also observed that these acids were not effective against adenovirus, which is a "naked" virus. Based on this, they concluded that these acids were effective in vitro against "enveloped" viruses but not against "naked" viruses. In vivo, an acid solution would not work, as it is unable to penetrate the outer dermal layer and so cannot get to the virus where it is replicating.

The use of certain alcohols (chain lengths carbons) to inactivate lipid-containing viruses is disclosed by W. Snipes et al. (Antimicrobial Agents and Chemotherapy, 11(1), pp. 98-104, (1977)). Although the authors used alcohols ranging from C4 to C18, they point out that a striking peak in virucidal activity was found for saturated alcohols having chain lengths from 10 to 14 carbons. Since longer-chain alcohols having 10 carbons or more are extremely insoluble in aqueous media, the preferred C10-C14 alcohols first had to be prepared in 95% ethanol at 100 times the desired final concentration. The final treatment was in solutions adjusted to a pH of at least 7.2. Thus, although the C10-14 alcohols were shown to have good virucidal action, their relatively low water solubility is a disadvantage in view of the initial preparation steps required.

Konowalchuk et al. reported a 1000-fold reduction in poliovirus infectivity after incubation with grape juice, at the natural pH of the wine (pH 3.3-4.4) or at pH 7.0 for 24 hours at 4° C., and found that commercial grape juice at neutral pH inactivated the herpes simplex virus. Red wines were reported to be more antiviral than white wines. The effect of wine at its natural pH against the herpes simples virus was not examined.

Noda et al. (J. Jap. Ass. Infect. Dis. 55, 355-366 (1981)) have reported that pure methanol, ethanol, n-propanol, isopropanol or butanol have distinct but limited virucidal effects in vitro in very high concentrations of around 80% or more. Lower concentrations of these alcohols were not sufficiently effective. Individually, pure propanol, isopropanol or butanols were not sufficiently active against "naked" hydrophilic viruses. Known mixtures of ethanol and isopropanol with a total active-substance content of 20 to 40% also show no virucidal activity.

Von Rheinbaben, et al. (U.S. Pat. No. 5,728,404) disclose compositions having virucidal activity against "naked" viruses (e.g., polio, adeno, vaccina, and SV40 tumor virus) comprising 50% to 90% by weight of at least one member selected from the group consisting of $C_1$-$C_4$ aliphatic monohydric alcohols and from 0.1% to 1.0% by weight of at least one metal salt, such as a zinc salt. Von Rheinbaben et al. found that compositions comprising between 40-80% by weight of ethanol, n-propanol, isopropanol, butanol, or mixtures thereof were ineffective against polio, adeno, vaccinia, and SV40 tumor viruses; however, these compositions could be made virucidal by adding metal salts to these alcoholic compositions.

Revici et al. (U.S. Pat. No. 4,513,008) disclose a method of inactivating an enveloped virus (HSV-2) comprising contacting the virus with a virucidally effective amount of a $C_{20}$-$C_{24}$ linear polyunsaturated acid, aldehyde or primary alcohol having 5-7 double bonds.

Brown-Skrobot et al. (U.S. Pat. No. 4,975,217) disclose a composition having germicidal activity when applied to hands contaminated with *Serritia marcescens*, a gram-negative bacteria, wherein the composition consists essentially of an anionic surfactant (e.g., an alkyl sulfonate salt) and an organic acid (malic acid, citric acid, and mixtures thereof). Brown-Skrobot et al. states that the surfactant alone and the acid alone showed no germicidal activity, and emphasize that both the organic acid and the anionic surfactant must be used to achieve significant germicidal activity. Alcohol was mentioned as an optional ingredient in the Brown-Skrobot et al. composition. Brown-Skrobot et al. did not test the effectiveness of this composition against viruses.

Hoffler, et al. (U.S. Pat. No. 5,043,357) disclose compositions having virucidal activity against naked viruses (e.g., poliovirus type 1), having at least 70% by weight of ethanol and/or propanols and from 0.5% to 5% by weight of a shortchain acid. Ethanol and propanol alone did not exhibit sufficient activities against the naked viruses. These compositions were not tested for their effectiveness against enveloped viruses, nor were the virucidal activities of the compositions tested in vivo.

Hendley et al. (U.S. Pat. No. 6,034,133) disclose a hand lotion effective against the naked rhinovirus, containing malic acid, citric acid, and a $C_1$-$C_6$ alcohol for preventing hand-to-hand transmission to rhinoviruses. Hendly et al. states that the lotions retain their virucidal activity as long as the concentration of the alcohol in the lotion is between 25-90%. The pH of the lotion is adjusted to be between pH 3 and pH 6 to avoid irritating the skin.

Dove, et al. (U.S. Pat. No. 5,071,650) disclose an in vitro method of inactivating viruses such as VSV (a lipid-coated virus) present in a aqueous solution of biologically active protein (e.g., plasma or cell cultures) by treating the solution with an intermediate length alcohols (C4-C 10) at a pH of about 4 to 5 at a temperature of 4° C., with virucidal activity increasing with increasing carbon chain length up to C8. Ethanol and butanol were found to be fairly inactive under these conditions.

Recently, the FDA has approved docosanol (10% cream) as a treatment for recurrent oral-facial herpes (cold sores and fever blisters) (see Katz et al., U.S. Pat. Nos. 5,952,392 and 5,534,554). Because of the low water solubility of this long chain (C26) alcohol, the composition requires a difunctional block-polymer nonionic surfactant in order to produce a suspension or emulsion of the docosanol. Further, in U.S. Pat. No. 5,534,554, supra states that certain excipients were detrimental to the activity of n-docosanol, and stress that the preparation of stable, effective n-docosanol-containing compositions presented an unexpectedly difficult challenge.

A need continues to exist for topical compositions which are active against enveloped and naked viruses and which have very low toxicity, especially one that is a potent topical virucide against herpes simplex virus that is inexpensive and easy to use.

SUMMARY OF THE INVENTION

These and other needs are satisfied by the present invention which provides virucidal compositions which are highly effective over a broad spectrum of enveloped viruses and yet can be produced and used with safety.

More specifically, this invention provides a method utilizing compositions of this invention for topical application for the prevention and treatment of symptoms associated with herpes simplex infections and other envelope virus infections. These compositions are primarily for application to the lips in treatment of cold sores, to the skin for the treatment of Herpes infections and to the surrounding skin of the penis, vagina or rectum for treatment and prevention of Herpes simplex infections. It is proposed, however, that these compositions can also be applied to other parts of the organism, for example to the oral, vaginal and rectal cavities, as well as surrounding tissue. Furthermore, the compounds may be used in fluids used to kill virus on instruments and surfaces such as examining tables, gloves, towels and other surfaces which might come in contact with the animal or human body during the course of medical and dental examinations, and as safe antiviral disinfectants in a clinical environment.

In one aspect, the present invention provides virucidally effective compositions consisting essentially of an aqueous solution of a short chain alcohol or diol adjusted to a pH at or below 4.6 with a suitable acid. Preferred such compositions suitable for topical application are also provided.

In another aspect, the present invention provides a method of inactivating enveloped virus, which comprises contacting the site of said virus or the virus itself with a virucidally effective amount of a composition of this invention.

In another aspect, the present invention provides a method of treating lesions associated with a herpes infection in an animal or human subject, which comprises applying to the inflamed area an amount of a virucidal composition of the invention effective for reducing or arresting such lesions.

In another aspect, the present invention provides a method of preventing lesions associated with a herpes infection in an animal or human subject, which comprises applying to the inflamed area an amount of a virucidal composition of the invention effective for preventing formation of such lesions.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

DETAILED DESCRIPTION OF THE INVENTION

The present invention provides compositions having virucidal activity against herpesvirus. As used herein, the term "herpesvirus" refers to any virus belonging to the family Herpesviridae, including herpes simplex virus, varicella-zoster virus, cytomegalovirus, and Epstein-Barr virus.

More specifically, the present invention provides topical compositions for preventing or reducing the viral lesions associated with herpes simplex virus infections or to shorten the time of healing. Herpes simplex refers to a variety of infections caused by herpesvirus types 1 and 2. Type 1 infections are marked most commonly by the eruption of one or more groups of vesicles on the vermilion border of the lips or at the external nares, and type 2 infections are marked by such lesions on the genitalia.

The compositions of this invention comprise a dilute aqueous solution of a C1 to C3 10 monohydroxy alcohol or a C3 to C4 diol which has been adjusted to a pH of 4.6 or below by the addition an inorganic or an organic acid. In one embodiment, the compositions are buffered, preferably with a suitable buffer that will maintain the pH of the composition. Such buffers are known to persons skilled in the art.

In preferred embodiments, the compositions comprise aqueous solutions having between about 0.2% and 13% by volume of the alcohol, more preferably between about 5% and 10% by volume of the alcohol in water, which have been adjusted to a pH of 4.6 or below by the addition of an inorganic or an organic acid. Suitable alcohols include short chain alcohols and diols, including methanol, ethanol, n-propanol, 2-propanol, 1,2-propanediol, 1,3-propanediol, 1,2-butanediol, 1,3-butanediol, 1,4-butanediol, and 2,3-butanediol.

Inorganic acids which may be used in the compositions of this invention include, but are not limited to, hydrochloric, chlorous, sulfuric, hypochlorous, hypophosphorous, iodic, nitrous, periodic, phosphoric, phosphorous, and sulfurous acids. Preferably the inorganic acid is hydrochloric acid.

A preferred composition of this invention comprises 10% by volume of ethanol or 95% ethanol in water, wherein the pH of the composition is adjusted to a pH of 4.6 or below by the addition of glycolic acid or HCl. For example, the pH may be adjusted to 4.6 by the addition of a 0.6% aqueous glycolic acid solution or a 0.1M HCl solution.

The compositions of the present invention contain ingredients, i.e., an alcohol and an acid, which by themselves are not potent antivirals when applied topically to the site of infection. For example, it is known that certain organic acids such as dicarboxylic acids are virucidal in vitro but are ineffective when applied topically. In addition, lower chain alcohols such as ethanol and propanol are known to be ineffective against enveloped viruses both in vitro and in vivo. Surprisingly, however, a synergistic antiviral effect is noted when these ingredients (i.e., an organic or inorganic acid and a $C_1$-$C_3$ alcohol or $C_2$-$C_4$ diol,) are used in combination in the compositions of this invention. That is, the inventor discovered that when an enveloped virus such as Herpes Simplex Virus type 1 (HSV-1) is contacted with an effective amount of a virucidal composition of this invention having a pH at or below 4.6, the virus is substantially inactivated, thereby interrupting and preventing the spread of the virus.

Thus, in contrast to the teachings of the prior art, which indicate that either an intermediate length alcohol (e.g., C-8 to C-26) and/or high concentrations of the alcohol (especially in the case of short chain alcohols) is required for virucidal activity, the inventor has discovered that dilute aqueous compositions comprising short chain alcohols can be used in virucidal compositions when used in combination with an organic or inorganic acid, wherein the acid is added in an amount that adjusts the pH of the composition to a pH of 4.6 or below.

The topical compositions of this invention were found to be active in vivo against HSV-1 (causing cold sores and fever blisters), HSV-2 (causing genital herpes) and herpes zoster (causing shingles). However, it is believed that these compositions will be active against other viruses in the Herpesviridae family, which are similar in structure or mechanism of infection, including the varicella virus (causing chicken pox). Evidence of the efficacy of the virucidal compositions of the invention against HSV-1 both in vitro and in vivo has been obtained using standard assay procedures as described below in the Examples.

Table 1 shows of time required for growth inhibition of herpes simplex virus 1 (HSV-1) using various concentrations of aqueous ethanol solutions adjusted to pH 3.5 by the addition of 0.1N or 1.0N HCl, both when the solutions were not diluted and after diluting the solutions by ¼, ¹⁄₁₆, or ¹⁄₆₄ with Eagles medium. The experiments were performed as described in Example 1.

TABLE 1

| | 5 minute exposure | | | | 10 minute exposure | | | |
|---|---|---|---|---|---|---|---|---|
| % ethanol | undiluted | ¼ | ¹⁄₁₆ | ¹⁄₆₄ | undiluted | ¼ | ¹⁄₁₆ | ¹⁄₆₄ |
| 1.0 | + | + | + | + | − | + | + | + |
| 2.5 | + | + | + | + | − | − | + | + |
| 5.0 | + | + | + | + | − | − | + | + |
| 10 | + | + | + | + | − | − | + | + |
| 12.5 | − | − | + | + | − | − | − | + |

+: Virus growth
−: no virus growth

As shown in Table 1, only the 12.5% ethanol solution inhibited the virus after an exposure time of five minutes. However, when the exposure time was increased to 10 minutes, even fairly dilute compositions (e.g., the 2.5% ethanol solution diluted by 1/4) effectively inhibited growth of the virus.

Next, various aqueous acid solutions were tested for the virucidal activity as shown in Table 2. The glycolic acid solution having a pH of 3.8 was prepared by preparing a 0.6% by weight solution of glycolic acid in water, and the remaining glycolic acid solutions were prepared by adjusting pH of the 0.6% glycolic acid solution by the addition of 0.1N or 1.0N sodium hydroxide. The succinic acid solution was a 0.2% by weight solution of succinic acid in water.

TABLE 2

Effect of pH on the growth of HSV-1 after an exposure of 4 minutes.

| | | Virus growth at sample dilution | | | |
|---|---|---|---|---|---|
| Acid | pH | Undiluted | ¼ | ¹⁄₁₆ | ¹⁄₆₄ |
| glycolic acid | 3.8 | − | − | − | − |
| glycolic acid | 4.0 | + | + | + | + |
| glycolic acid | 6.0 | + | + | + | + |
| succinic acid | 4.2 | − | + | + | + |

+: virus growth
−: no virus growth

In another experiment, various alcohols at concentrations of 0.2% by volume were adjusted to various pH's to determine the upper limit of the pH that is required for each alcohol in order for the acidic alcohol solution to exhibit antiviral activity against HSV-1. Samples of each alcohol at pH 4.0 to 6.8 at increments of 0.2 pH units were incubated with the virus for 2 minutes and then plated as described in Example 1. That is, each of the alcohols in Table 3 were tested at pH 4.0, 4.2, 4.4, 4.6, 4.8, 5.0, 5.2, 5.4, 5.6, 5.8, 6.0, 6.2, 6.4, 6.6 and 6.8. The pH was adjusted using 0.1N or 1.0N HCl. Methanol, n-butanol, and 2,3-butanediol were effective in completely inactivating HSV-1 up to a pH of 4.6, ethanol was effective up to a pH of 4.4, and 1,2-butanediol was effective up to a pH of 4.2.

TABLE 3

Upper pH limit at which HSV-1 is inactivated by the alcohol

| Alcohol | Concentration of alcohol | Upper limit of pH |
| --- | --- | --- |
| methanol | 0.2% | 4.6 |
| ethanol | 0.2% | 4.4 |
| n-butanol | 0.2% | 4.6 |
| 1,2-butanediol | 0.2% | 4.2 |
| 2,3-butanediol | 0.2% | 4.6 |

It is well known in the art that ethanol or propanols alone have no virucidal activity against enveloped viruses. While not wishing to be bound by any particular theory, it is believed that the alcohol facilitates penetration of the acid through the outer dermal layer to the site of HSV replication. That is, a synergy was observed between the acid and the alcohol, in that it was found that both must be used to achieve significant topical virucidal activity. Further, it was discovered that the pH of the composition determined the virucidal effect of the composition greater that the acid used to lower the pH of the compositions. Thus, the low pH compositions of this invention are better able to penetrate to the deeper, infected layers of the skin better than the individual components alone, thus enhancing the effectiveness of the alcohol and/or the acid to inactive the virus. For example, without the alcohol, the acids may not penetrate the tissue to allow effective action against the virus. It is for the purposes of enhancing the penetration and extending retention time of the acid that the short chain alcohols are used in the virucidal compositions of this invention.

A further advantage of the compositions of this invention is that the short chain alcohols avoid the insolubility problems as well as the unpleasant odors associated with alcohols having longer chain lengths The compositions were evaluated for the treatment of recurrent oral-facial herpes simplex infections as described in Example 2. A group of patients applied a solution consisting essentially of 10% by volume ethanol (95%) and 0.6% by weight glycolic acid in water, adjusted to pH 2.45, at the time of erytherna, papule or vesicle stages. Development of blisters was arrested and rapid crusting of the vesicles occurred within 2 to 3 days of treatment, as compared to 10 or more days without treatment. When the same composition was applied within 24 hours of the prodromal stage of infection, that is, during awareness of burning, tingling, or itching but before blister development, the subjects noted that development of a papule did not occur. Thus, the compositions of the invention appear to prevent the formation of lesions, as well as being effective in reducing the healing time of the lesions.

Another patient suffering from recurrent herpes zoster of the face applied a composition of this invention comprising 13.5% ethanol mixed with aqueous glycolic acid to give the composition a pH of 3.1. The composition was applied 3 times in 20-minute intervals. The herpes zoster lesion healed in 2 days, in contrast to a previous outbreak in the same patient, which lasted 3 months.

The virucidal compositions of this invention can be administered singly or as divided dosages throughout the day. For the control of HSV-1 infections, application of a virucidally effective amount of a composition according to the invention to an infected area, e.g., skin surfaces such as the area around the mouth, lips, mucous membranes, eyes, of an animal or human subject suffering from a viral infection, especially a herpes infection, will generally range from about one to three applications per day, depending upon the area to be treated, the severity of the symptoms and the nature of the virucidal agent and the topical vehicle employed. A preferred topical preparation is an acidic alcohol solution wherein about 0.2 to 13% of the alcohol is used per milliliter of water or buffer, wherein the pH of the solution has been adjusted by the acid to a pH at or below 4.5, and preferably to a pH of about 2.6. The compositions of this invention are administered topically to the locus to be protected or treated by immersing, spraying or swabbing said locus.

For the control of genital herpes; i.e., HSV-2 infections, the compositions of this invention are administered intravaginally preferably in admixture with a pharmaceutical carrier. The carrier is, of course, chosen with regard to the intended route and method of administration. In the present invention administration is accomplished topically; i.e., to a definite place or locus, in this instance, for example, the vagina, in the form of a cream, ointment, foam, jelly, tablet, ovule or other suitable composition which lends itself to a topical vaginal dosage form. Creams and ointments are preferred forms.

A preferred mode of application of the virucidal compositions of the invention is as a topical agent. Preferably, the topical agent is a solution, that is, a liquid formulation comprising the aqueous alcohol and the acid. Other suitable forms include semi-solid or solid forms comprising a carrier indigenous to topical application and having a dynamic viscosity preferably greater than that of water, provided that the carrier does not deleteriously react with the acid or the alcohol in the composition. Suitable formulations include, but are not limited to, lip balms, suspensions, emulsions, creams, ointments, powders, liniments, salves and the like. If desired, these may be sterilized or mixed with auxiliary agents, e.g., preservatives, stabilizers, wetting agents, buffers or salts for influencing osmotic pressure and the like. Preferred vehicles for semi-solid or solid forms topical preparations include ointment bases, e.g., polyethylene glycol-1000 (PEG-1000); conventional ophthalmic vehicles; creams, e.g., HEB cream; and gels, e.g., K-Y gel; as well as petroleum jelly and the like. These topical preparations may also contain emollients, perfumes and/or pigments to enhance their acceptability for various usages, provided that the additives do not deleteriously react with the acid or the alcohol in the composition.

Also suitable for topical application are sprayable aerosol preparations wherein the virucidal compound, preferably in combination with a solid or liquid inert carrier material, is packaged in a squeeze bottle or in admixture with a pressurized volatile, normally gaseous propellant, e.g., a Freon (chlorofluorocarbon) or environmentally acceptable volatile propellant. Such compositions can be used for application to environmental surfaces, e.g., examining tables, toilet seats and the like, and/or for application to the skin or to mucous membranes. The aerosol or spray preparations can contain solvents, buffers, surfactants, perfumes and/or antioxidants in addition to the virucidal compounds of the invention.

The compositions of this invention can be employed in mixture with conventional excipients, i.e., pharmaceutically acceptable organic or inorganic carrier substances suitable for topical application which do not deleteriously react with the acid or the alcohol in the composition. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, lubricants, preservatives, stabilizers, wetting agents, emulsifiers, salts for influencing osmotic pressure, buffers, coloring, flavoring and/or aromatic substances and the like which do not deleteriously react with the acid or the alcohol in the composition.

The virucidal properties of the compounds of the invention suggest their use to prevent the spread of infection by enveloped virus, e.g., by incorporating them in a hand cream or lotion for use by physicians both before and after the examination of patients with suspected virus infections. Furthermore, the compounds may be used in fluids used to kill virus on examining tables, instruments, gloves, towels and other surfaces which might come in contact with virus particles during the course of medical examinations. Further, all of the ingredients employed in the compositions of this invention are generally recognized as safe. The low toxicity of the compounds of the invention further enhances their attractiveness for such prophylactic use.

EXAMPLES

Example 1

Growth Inhibition of HSV-1 in vitro Using Various Alcohol Concentrations at pH 3.5

The following ethanol solutions were made by diluting 95% ethanol with Eagles medium (pH 4.2): 1%, 2.5%, 5%, 10% and 12.5%. The pH was adjusted with 0.1N HCl or 1.0N HCl to pH 3.5. Each solution was also diluted by ¼, ¹⁄₁₆ and ¹⁄₆₄ with Eagles medium as shown in Table 1.

The assay is performed upon Vero African green monkey kidney cells which have been grown in polypropylene 12-well trays in Eagles minimum essential nutrient medium. The trays were incubated until a monolayer of cells had fully grown across the bottom of the tray. Each tray slot contains approximately 2 mL of Eagles medium adjusted to a pH of 7.

The virus was collected from a subject with an active Herpes Type 1 lesion. The sample was inoculated into a flask containing Vero cells grown in Eagles medium, pH 7.3. After the virus had infected all cells, the flask was frozen and thawed several times to burst the cells and release the virus. The contents were centrifuged to remove the cellular debris and the supernatant containing the virus was dispensed into ampules and stored at −20° C. for short term storage. One thawed virus ampule was diluted in Eagles medium, pH 4.1, so that 0.25 mL contained sufficient virus to form 25-50 plaques per well in the virus controls.

The alcohol solution to be tested for activity was dissolved in Eagles medium, adjusted to pH 4, then serially diluted ¼, ¹⁄₁₆, ¹⁄₆₄, etc. in Eagles medium. Virus was added, 0.25 mL per sample dilution, and held for the specified period. Two drops from a Pasteur pipette were then added to each of two wells in the plate. After 3 days of incubation, the wells were examined for cytopathic effect. Control wells should show 25-50 plaques.

Example 2

In vivo Inhibition of HSV-1

Three human subjects having history of acute recurrence of herpes labialis with a reported average duration of untreated episodes lasting ten days applied a solution prepared by combining 10 mL of 95% ethanol, 0.6 g glycolic acid, and 90 mL distilled water, wherein the final pH of the solution was 2.45, to affected areas once every 20 minutes for a minimum of three times daily during a 24 hour period. The material was dabbed on by finger and allowed to air dry between applications. When applied at the time of erythema, papule or vesicle stages, development was arrested and rapid crusting of vesicles occurred. Complete healing occurred when the crust fell off spontaneously or there was no longer evidence of an active lesion. These data show that the duration of cold sores decreased significantly to an average of 2 days following the above-described treatment.

When the same composition was applied within 24 hours of awareness, i.e., burning, tingling or itching, further development did not occur. The usual edema and pain accompanying herpes eruptions was eliminated.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising", "include," "including," and "includes" when used in this specification and in the following claims are intended to specify the presence of stated features, integers, components, or steps, but they do not preclude the presence or addition of one or more other features, integers, components, steps, or groups thereof.

We claim:
1. A topical composition for inactivating an enveloped virus at a site of infection, said composition consisting of:
    (i) an alcohol selected from the group consisting of 2,3-butanediol, 1,2-butanediol, 1,3-butanediol, and 1,4-butanediol;
    (ii) a sufficient amount of an organic acid to adjust the pH of the composition to between 2.45 and 4.5; and
    (iii) a pharmaceutically acceptable carrier.
2. The composition of claim 1, wherein said organic acid is selected from the group consisting of glycolic acid, lactic acid, succinic acid malic acid, citric acid, and acetic acid.
3. The composition of claim 1, wherein the pH of said composition is 2.45.
4. The composition of claim 1, wherein the concentration of said alcohol is between about 0.2% and 12.5% by volume.
5. A topical composition for inactivating an enveloped virus, said composition consisting of:
    (i) an alcohol having a concentration of 0.2 to 13.0% by volume in water;
    (ii) a sufficient amount of an acid to adjust the pH of the composition to between 2.45 and 4.6; and
    (iii) a pharmaceutically acceptable carrier, wherein said alcohol is selected from the group consisting of methanol, 1-propanol, 2-propanol, 2,3-butanediol, 1,2-butanediol, 1,3-butanediol, and 1,4-butanediol.
6. A topical composition for inactivating an enveloped virus, said composition consisting of:
    (i) a C2-C4 diol having a concentration of 0.2 to 13.0% by volume in water;
    (ii) a sufficient amount of an acid to adjust the pH of the composition to between 2.45 and 4.6; and
    (iii) a pharmaceutically acceptable carrier, wherein said acid is selected from the group consisting of glycolic acid, lactic acid, succinic acid, malic acid, citric acid, acetic acid, and hydrochloric acid.
7. A topical composition for inactivating a virus selected from the group consisting of herpes simplex 1 virus, herpes simplex 2 virus, and Varicella-zoster virus, said composition consisting of:
    (i) an alcohol having a concentration of 0.2 to 13.0%, by volume in water, said alcohol selected from the group consisting of methanol, 1-propanol, 2-propanol, 2,3-butanediol, 1,2-butanediol, 1,3-butanediol, and 1,4-butanediol;

(ii) a sufficient amount of an acid to adjust the pH of the composition to between 2.45 and 4.6, wherein said acid is selected from the group consisting of glycolic acid, lactic acid, succinic acid, malic acid, citric acid, acetic acid, and hydrochloric acid; and (iii) a pharmaceutically acceptable carrier.

* * * * *